United States Patent
Sotoyama et al.

(10) Patent No.: US 6,673,311 B1
(45) Date of Patent: Jan. 6, 2004

(54) METHOD AND APPARATUS FOR CONTINUOUS HEAT STERILIZATION OF LIQUID

(75) Inventors: Kazuyoshi Sotoyama, Kanagawa (JP); Keiji Iwatsuki, Kanagawa (JP); Teruhiko Mizota, Kanagawa (JP); Yuzo Asano, Kanagawa (JP); Yasutatsu Mizota, Kanagawa (JP); Hiroaki Matsui, Kanagawa (JP); Tetsushi Mori, Kanagawa (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 0 days.

(21) Appl. No.: 09/529,956
(22) PCT Filed: Oct. 16, 1998
(86) PCT No.: PCT/JP98/04680
§ 371 (c)(1),
(2), (4) Date: Jun. 26, 2000
(87) PCT Pub. No.: WO99/21442
PCT Pub. Date: May 6, 1999

(30) Foreign Application Priority Data

Oct. 23, 1997 (JP) .............................................. 9-309259

(51) Int. Cl.[7] ................................................. A61L 2/00
(52) U.S. Cl. .............................. 422/1; 99/453; 99/461; 422/26; 422/39; 422/295; 426/521
(58) Field of Search ............................ 422/26, 39, 295, 422/1; 99/453, 461; 426/521

(56) References Cited

U.S. PATENT DOCUMENTS

| | | | | |
|---|---|---|---|---|
| 5,503,064 A | * | 4/1996 | Scheel et al. | 99/453 |
| 5,658,610 A | * | 8/1997 | Bergman et al. | 426/665 |
| 6,004,508 A | * | 12/1999 | Platz et al. | 422/26 |
| 6,120,732 A | * | 9/2000 | Toledo et al. | 422/39 |
| 6,162,392 A | * | 12/2000 | Platz et al. | 422/26 |

* cited by examiner

Primary Examiner—Krisanne Thornton
(74) Attorney, Agent, or Firm—Wenderoth, Lind & Ponack, L.L.P.

(57) ABSTRACT

A method for continuous heat sterilization of liquid includes a continuous pre-heating step of preheating the liquid, a final heating step of heating the preheated liquid to reach a predetermined sterilizing temperature, a holding step of holding the liquid which has reached the predetermined sterilizing temperature for a predetermined period of time, and a cooling step of cooling the held liquid. The final heating step comprises the following steps (a) and (b): (a) a step of continuously pressurizing the liquid by a high pressure pump; and (b) a step of releasing the liquid continuously to a normal pressure within a time period of less than 10 seconds after the pressurizing step to thereby make the liquid reach the predetermined sterilizing temperature. An apparatus for automatically carrying out the method is provided. According to the continuous heat sterilization method and apparatus, scorch during the final heating step is dispensed with and accordingly, a long period of continuous operation is feasible. Furthermore, denaturation of liquid caused by heating is inconsiderable, investment cost and running cost become inexpensive, and a large amount of liquid can be processed.

26 Claims, 6 Drawing Sheets

METHOD AND APPARATUS FOR CONTINUOUS HEAT STERILIZATION OF LIQUID

TECHNICAL FIELD

The present invention relates to a method and apparatus for continuous heat sterilization of liquid. Particularly, the present invention relates to a method for continuous heat sterilization of liquid including a preheating step, a final heating step, a retaining step and a cooling step, and to an apparatus for performing this method.

BACKGROUND ART

Conventionally, as a sterilizing method for food, there has been widely adopted a heat sterilization method for heating food at high temperatures. Food is classified into liquid-like food or solid-like food, depending on whether convection is predominant or conduction is predominant in a mechanism of heat transfer when the food is heated, and is also classified into paste-like food as food showing properties between properties of liquid-like food and solid-like food.

As methods of heat sterilization of liquid-like or paste-like food, there is a pre-filling sterilizing method in which food is heated and sterilized before being filled into a container, filled and hermetically sealed in the container while remaining at high temperatures, cooled in a sterilized manner and filled in a sterilized atmosphere into the container in a sterilized state. There is also a post-filling sterilizing method in which food is filled into a container, hermetically sealed, and thereafter heated along with the container to thereby sterilize the food. Further, the former pre-filling sterilizing method is classified into a case in which food is continuously heated, and a case in which food is batch heated by a double can (refer to "Food Engineering Basic Course, volume 10, Food Reaction Engineering", Kiyoshi Kubota et al., page 111, Korin Kabushiki Kaisha, Sep. 29, 1990).

Generally, when liquid as in liquid-like food or paste-like food is heated and sterilized, there is carried out a continuous heat sterilization method of an HTST method, a UHT method or the like in which mass processing is feasible. An explanation will be given of an example of a conventional continuous heat sterilization method of liquid with reference to FIG. 4. FIG. 4 is a schematic view for explaining an example of a conventional continuous heat sterilization apparatus for liquid.

In FIG. 4, a conventional apparatus 1c for continuous heat sterilization of liquid includes a feed pump 3 connected to a storage tank 2 for liquid. In FIG. 4, a rotary type constant amount pump is used as the feed pump 3. Although the feed pump of FIG. 4 is formed with a pipe for returning liquid from an outlet pipe to an inlet pipe, and the pipes are installed with a flow regulating valve, illustration thereof is omitted in FIG. 4. By returning liquid from an outlet side to an inlet side of the feed pump by the pipes, and regulating an amount of return by the flow regulating valve, pressure on an outlet side of the feed pump or a flow rate of pressure-fed liquid is regulated. On the outlet side of the feed pump 3, there is formed a flow pass of liquid connected with a preheating section 10, a low pressure homogenizer 20, a final heating section 35, a holding pipe 4, a first cooling section 40, a second cooling section 50 and a back pressure regulating valve 5 in this order, and a sterilized liquid outlet 6. Further, all of the preheating section 10, the final heating section 35, the first cooling section 40 and the second cooling section 50 for carrying out heat exchange are constituted by plate type heat exchangers.

Liquid stored in the storage tank 2 is pressure-fed to the preheating section 10 by the feed pump 3. In the preheating section 10 steam is introduced from a steam source 11 and subjected to heat exchange with liquid, and liquid is preheated to reach a predetermined preheating temperature. A temperature sensor 14 is installed at an outlet of the preheating section 10, an opening amount of a steam regulating valve 15 is regulated in accordance with temperature of liquid, and a temperature of liquid is controlled to a predetermined preheating temperature. The preheating temperature is generally about 40° to 90° C. Vapor-condensed water resulting from heat exchange is discharged via a trap pipe 12 or a discharge pipe 13. Liquid reaching the predetermined preheating temperature is pressure-fed to the low pressure homogenizer 20. A preheating step is carried out by the preheating section 10.

As a principle, the low pressure homogenizer 20 is provided when liquid includes fat, and is an apparatus for homogenizing the liquid by destructing fat balls in the liquid. Generally, a homogenizer is installed with a high pressure pump and a homogenizing valve (not illustrated), in either of a case of a low pressure homogenizer and a high pressure homogenizer, mentioned later. A high pressure pump is an apparatus in which a pressurizing chamber of a predetermined volume, having an inlet and an outlet for liquid, is provided with a plunger reciprocating in directions for increasing and decreasing the volume of the pressurizing chamber, and check valves are installed at the inlet and the outlet of the pressurizing chamber. Volume of the pressurizing chamber is increased and decreased by reciprocation of the plunger, and the check valves are naturally opened and closed in accordance with an increase and decrease of the volume to thereby suck and deliver liquid.

A homogenizing valve is a kind of a throttle valve for regulating a clearance of a flow pass for liquid delivered from a high pressure pump. That is, the homogenizing valve pressurizes liquid by throttling the clearance of the flow pass for liquid. Further, the homogenizing valve makes liquid pressurized in this way pass in a narrow flow pass and releases it to normal pressure, and destructs fat balls in the liquid during this occasion. Generally, pressure caused by narrowing a flow path by a homogenizing valve is referred to as homogenizing pressure. As a principle, homogenizing pressure of the low pressure homogenizer 20 is regulated within a range of from about 2 to 40 MPa.

Further, the low pressure homogenizer 20 is provided with a hydraulic control unit 21. The hydraulic control unit 21 is provided with a hydraulic pump and a hydraulic valve (both of which are not illustrated). Pressure is applied to oil by the hydraulic pump, the pressure is regulated by the hydraulic valve and thereafter, a homogenizing valve is operated by pressure of the oil to thereby regulate homogenizing pressure.

Generally, it is preferable to carry out a homogenizing operation with liquid at high temperature, and the low pressure homogenizer 20 is frequently provided downstream of the preheating section 10, however, there is a case in which the homogenizer 20 is installed downstream of the final heating section 35. In this case, liquid which comes out from the final heating section 35 is cooled, and thereafter made to pass through the low pressure homogenizer 20. Liquid passing through the low pressure homogenizer 20 is liquid after sterilization, and accordingly, the low pressure homogenizer 20 is to be sterilized. The low pressure homogenizer 20 specified to be sterilized, is provided with a structure in which, for example, steam or sterilized water is always supplied to seal portions of the plunger to thereby prevent contamination of liquid, and generally an apparatus cost and running cost are higher than those of an apparatus not specified to be sterilized. Further, the low pressure homogenizer 20 is installed with a bypass pipe 22 which is used only during cleaning for ensuring a flow rate of cleaning solution.

Liquid which comes out from such low pressure homogenizer 20 is fed to the final heating section 35. The final heating section 35 is a heat exchanger for elevating a temperature of liquid to a predetermined sterilizing temperature. The final heating section 35 is provided with a hot water producing device 36 which circulates hot water via a hot water circulating pass 37 to thereby heat liquid to reach the predetermined sterilizing temperature. A temperature sensor 33 is installed at an outlet of the final heating section 35 by which temperature of liquid is detected. Generally, a sterilizing temperature frequently falls within a range of from 90° to 160° C. A final heating step is carried out by the final heating section 35, mentioned above.

Liquid having reached the sterilizing temperature is flowed through the holding pipe 4. The holding pipe 4 is provided with a predetermined length and holds liquid for a predetermined period of time by which microorganisms in the liquid are exterminated.

This holding step is carried out by the holding pipe 4. Incidentally, temperature of liquid may be lowered by holding heat while flowing the liquid through the holding pipe 4, and is not necessarily maintained strictly at the sterilizing temperature; however, in the following explanation, an intermediary step, after the liquid has reached the sterilizing temperature and until the cooling step is carried out is regarded as the holding step.

Liquid with resulting from sterilization is fed to the first cooling section 40 and the second cooling section 50. In the first cooling section 40, water is fed from a water source 41 to a water pipe 42 to thereby cool liquid. In the second cooling section 50, cold water is fed from a cold water source 51 to a cold water pipe 52 to further cool liquid. Cooling steps are carried out by the first cooling section 40 and the second cooling section 50, mentioned above. Liquid resulting from the cooling steps is fed from the sterilized liquid outlet 6 to a succeeding step, for example, a sterilized filling step or the like.

Further, normally, in the final heating section 35, temperature of hot water in the hot water circulating pass 37 is regulated based on a detection value of the temperature sensor 33, and is automatically controlled to a predetermined sterilizing temperature. Furthermore, at the outlet of the final heating section 35, when temperature of liquid becomes lower than an allowable temperature range, an operation of automatically returning sterilized liquid back to the storage tank 2 is carried out; however, in FIG. 4, illustration of devices for this operation is omitted.

Further, generally, in the continuous heat sterilization apparatus shown by FIG. 4, for energy conservation, there is a case in which heat exchange is carried out between high temperature liquid after sterilization and low temperature liquid before sterilization. Further, as another example of the final heating section 35, there is a type in which steam is directly blown into liquid to thereby heat it, and in this case, a vacuum chamber is used in the first cooling section 40 and there is carried out an operation of cooling liquid by estimating blown steam. However, in the above-described heat sterilization method (hereinafter, described as Prior Art 1), liquid is frequently denatured by being heated and particularly when liquid to be sterilized is food, drugs, or raw materials of these, it is recognized that flavor is changed to some degree during a heat sterilization process.

In order to overcome such difficulties of heat sterilization, in recent years, there has been developed a high pressure sterilizing method. The high pressure sterilizing method is a method of exterminating microorganisms by holding liquid under high pressure, and there are known various technologies for performing such a sterilizing method, for example, technologies disclosed in JP-A-4-174669, JP-B-6-57236, JP-A-6-225707, JP-A-6-327445, JP-A-6-327446, JP-A-8140593, JP-A-8-196249, JP-A-57-22679, JP-A-4-91770, JP-B-7-28706 and JP-A-5-227925 (hereinafter, described as Prior Art 2).

Further, for the high pressure sterilizing method, particularly, as a method of using an ultra high pressure homogenizer, there is known a technology disclosed in JP-A-6-205655 (hereinafter, described as Prior Art 3).

Further, the inventors have invented a sterilizing method in which liquid is pressurized, thereafter press-fed to two divided flow passes, and injected from small holes opposed to each other to thereby collide with each other, by which sterilization is carried out, and the inventors have already filed an application patent (JP-A-7-298861, hereinafter, described as Prior Art 4).

However, in the above described Prior Art 1, as the final heating section 35, there is frequently used a heat exchanger of a type in which heat of a heat medium and liquid is transferred and received via a heat transmitting wall, for example, a plate type heat exchanger. Furthermore, there is frequently used a steam nozzle of a type in which steam is blown into liquid to thereby heat it, and accordingly, the following problems are posed.

i) In the final heating section 35, it is inevitable that scorch (scale) is adhered to a heat transmitting wall or the steam nozzle, and efficiency of heating is deteriorated with elapse of time.

ii) A period of operational time is restricted by scorching of the final heating section 35. That is, when a large amount of scorch is adhered to the final heating section 35, sterilizing processing needs to stop and accordingly, continuous operation for a long period of time is not possible.

iii) Particularly, in the case of a plate type heat exchanger, temperature is gradually elevated until liquid reaches a sterilizing temperature, and denaturation of liquid is progressed by excessive heating while a temperature of the liquid is elevating.

According to the high pressure sterilizing method of Prior Art 2 mentioned above, there poses a problem in which generally, pressurizing to a high pressure of at least 100 MPa is needed, and accordingly, an apparatus having high strength is needed. Furthermore, a time period of at least 1 minute is required, and therefore, as a whole, investment cost is enormous and an amount of processing is small, which is unsuitable for mass production. In other words, according to the above-described Prior Art 2, when a processing pressure is set low a processing time period is prolonged, and when a processing pressure is set high more strength of the apparatus is needed, and as a result, there is not present any apparatus suitable for mass production while investment cost is low.

According to an apparatus of using an ultra high pressure homogenizer of Prior Art 3, a homogenizing pressure is an ultra high pressure exceeding 100 MPa, and accordingly, a special exclusive homogenizer is needed. Further, an effect of sterilization is poor in comparison with that of heat sterilization, and accordingly, it is difficult to achieve complete extermination of bacteria, and a liquid having low pH of exclusively juice or the like is an object of the apparatus.

Although Prior Art 4 resolves the above-described problem, an apparatus having a slightly complicated structure is needed, and accordingly, a simpler method and apparatus have been long-awaited.

As a result of continuing intensivey research to improve the apparatus of Prior Art 4 so as to make it more simple, the inventors have discovered that this problem can be resolved by a simple apparatus using an on sale homogenizer, and have completed the invention.

It is an object of the invention to provide a method for continuous heat sterilization of liquid in which scorch during a final heating step is dispensed with, and accordingly, a long period of continuous operation is possible. Further, denaturation of liquid caused by heating is insignificant.

It is another object of the invention to provide an apparatus for continuous heat sterilization of liquid in which scorch during a final heating step is dispensed with, and accordingly, a long period of continuous operation is possible. Furthermore, denaturation of liquid caused by heating is insignificant. Still further, investment cost and running cost are low and an amount of processing is large.

SUMMARY OF THE INVENTION

According to a first aspect of the invention, there is provided a method for continuous heat sterilization of liquid, includes a continuous preheating step of preheating the liquid, a final heating step of heating the preheated liquid to reach a predetermined sterilizing temperature, a holding step of holding the liquid which has reached the predetermined sterilizing temperature for a predetermined period of time, and a cooling step of cooling the held liquid, wherein the final heating step comprises the following steps (a) and (b):

(a) a step of continuously pressurizing the liquid by a high pressure pump; and (b) a step of releasing the liquid continuously to a normal pressure within a time period of less than 10 seconds after the pressurizing step to thereby make the liquid reach the predetermined sterilizing temperature.

Preferable modes of the first aspect of the invention are that the steps (a) and (b) are carried out by a homogenizer (hereinafter, described as a first mode), and that during step (a) the liquid is pressurized within a pressure range of from 50 MPa to 100 MPa (hereinafter, referred to as a second mode), and that during step (b) the liquid is made to reach a temperature range of from 90° C. to 160° C. (hereinafter, described as a third mode).

According to a second aspect of the invention, there is provided an apparatus for continuous heat sterilization of liquid, which apparatus comprises a storage tank for storing the liquid, a feed pump for press-feeding the liquid stored in the storage tank, a preheating section for preheating the liquid press-fed by the feed pump, a pressurization release apparatus including a high pressure pump and a throttle valve for continuously pressurizing the liquid preheated by the preheating section and releasing the liquid preheated by the preheating section to a normal pressure continuously within a time period of less than 10 seconds to thereby reach a predetermined sterilizing temperature, a holding pipe for holding the liquid which has reached the predetermined sterilizing temperature, and a cooling section for cooling the liquid held by the holding pipe.

Preferable modes of the second aspect of the invention are that the continuous heat sterilization apparatus further comprises a temperature sensor provided at the holding pipe for detecting a temperature of the liquid coming out from the pressurization release apparatus, a controlling device for comparing a detection value detected by the temperature sensor with a previously inputted predetermined sterilizing temperature and calculating an operational amount for making the detection value and the predetermined sterilizing temperature approach each other, and a pressure regulating device for increasing or decreasing an amount of pressurization of the pressurization release apparatus in accordance with the operational amount calculated by the controlling device, whereby a temperature of the liquid coming out from the pressurization release apparatus is automatically controlled to the predetermined sterilizing temperature by the pressure regulating device (hereinafter, described as a fourth mode).

The continuous heat sterilization apparatus alternatively comprises a temperature sensor provided at the holding pipe for detecting a temperature of the liquid coming out from the pressurization release apparatus, a controlling device for comparing a detection value detected by the temperature sensor with a previously inputted predetermined sterilizing temperature and calculating an operational amount for making the detection value and the predetermined sterilizing temperature to approach each other, and a device for regulating a temperature of an inlet of the pressurization release apparatus for increasing or decreasing a temperature of the liquid on a side of the inlet of the pressurization release apparatus in accordance with the operational amount calculated by the controlling device, whereby a temperature of the liquid coming out from the pressurization release apparatus is automatically controlled to the predetermined sterilizing temperature by regulating a temperature of the liquid on the side of the inlet of the pressurization release apparatus (hereinafter, described as a fifth mode). Also, the pressurization release apparatus can be a homogenizer (hereinafter, described as a sixth mode).

DESCRIPTION OF THE PREFERRED EMBODIMENTS

Figure 1:
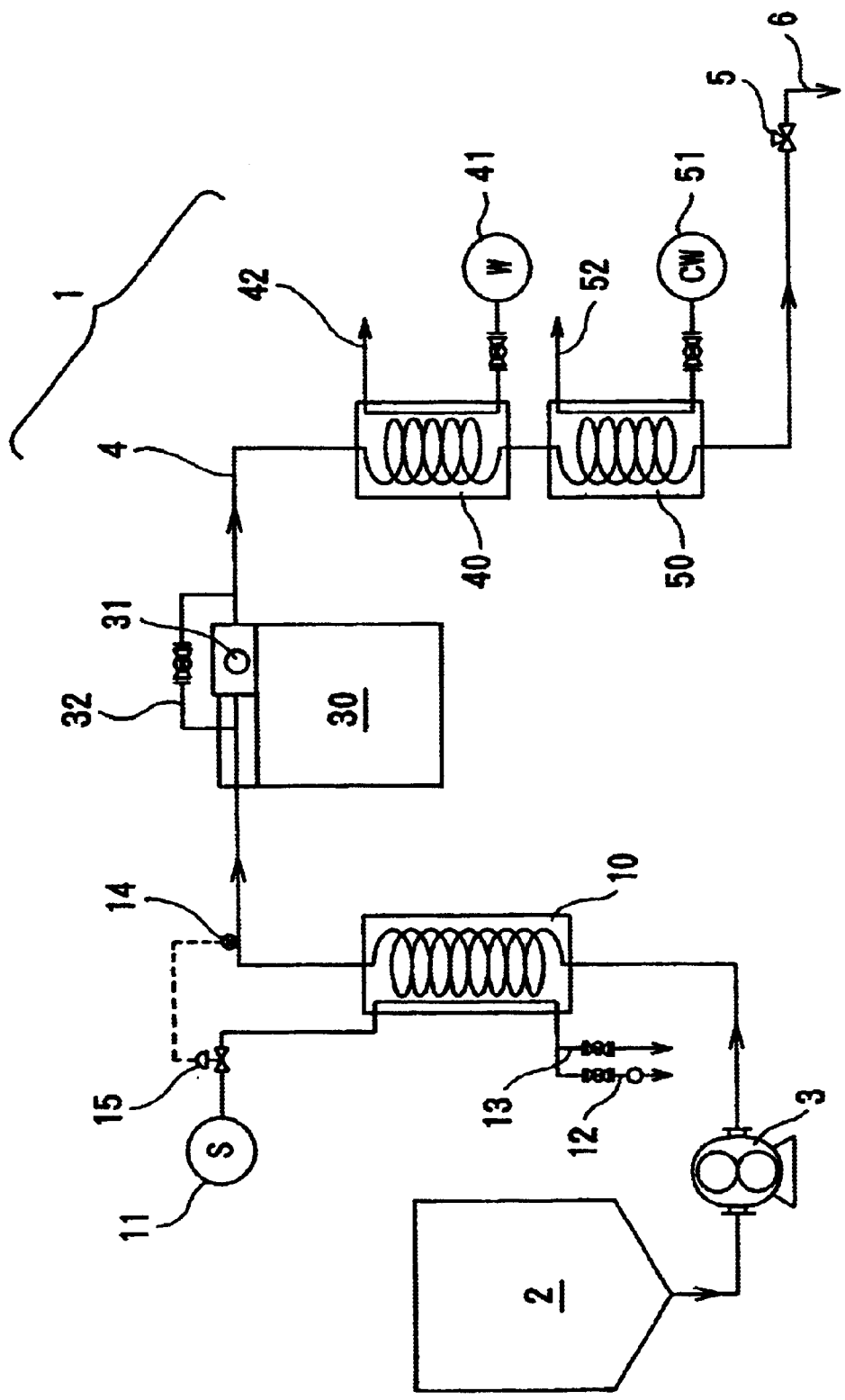
FIG. 1 is a schematic view showing an embodiment of a continuous heat sterilization apparatus for liquid according to the invention.

A first aspect of the invention comprises a preheating step, a final heating step, a holding step and a cooling step similar to the continuous heat sterilization method of Prior Art 1, mentioned above.

The preheating step is a step of elevating temperature of liquid prior to the final heating step. It is preferable that temperature of liquid after preheating falls to within in a range of 60° C. to 135° C.

During the final heating step, preheated liquid is continuously pressurized by a high pressure pump and successively released to normal pressure continuously to thereby reach a sterilizing temperature. When liquid is pressurized, pressure energy is stored in liquid. Thereafter, liquid is released to normal pressure in less than 10 seconds after pressurizing, more preferably, less than 5 seconds. Liquid released to normal pressure is jetted by converting pressure energy into kinetic energy, and kinetic energy is converted into heat to elevate temperature of liquid. During this occasion, the larger the pressure energy provided to liquid, the larger the amount of heating liquid, and accordingly, temperature of liquid can be regulated by increasing or decreasing a degree of pressurization.

According to a method of the invention, at least during a stage of making temperature of liquid reach a predetermined sterilizing temperature (that is, final heating step), it is preferable not to also use other heating devices substantially, and it is preferable that substantially there is no step of heating liquid after the final heading step until liquid is cooled.

In Prior Art 3, high pressure sterilization is carried out by pressurizing liquid, whereas according to the method of the invention pressurization and release is used exclusively for heating liquid. That is, conception of the method of the invention differs from that of Prior Art 3 in that liquid is made to reach a predetermined sterilizing temperature by pressurizing and releasing liquid. Further, liquid needs to be preheated to a suitable temperature before pressurization and release and as mentioned above, with this suitable temperature preferably falling within in a range of 60° C. to 135° C.

According to the method of the invention, liquid is released to normal pressure in less than 10 seconds after pressurization, more preferably in a time period of less than 5 seconds. In Prior Art 2, liquid needs to be exposed to high pressure for a long period of time to exterminate microorganisms by high pressure. However, according to the method of the invention, operation of pressurization and release is used only for heating, and accordingly, a time period of less than 10 seconds, more preferably, less than 5 seconds is sufficient. Accordingly, in the method of the invention, there is no need for a special apparatus for maintaining high pressure for a long period of time as in Prior Art 2.

According to the final heating step in the method of the invention, mentioned above, no heat is transmitted and received via a heat conducting wall as with a conventional heat exchanger, and steam is not blown into liquid by a steam nozzle, and accordingly, there is no phenomenon of scorching the heat conducting wall or the steam nozzle. Accordingly, efficiency of heat transfer is not lowered with elapse of time, and a long time period of continuous operation becomes feasible.

Further, according to the final heating step of the invention, temperature of liquid rises rapidly and reaches a sterilizing temperature substantially instantaneously from a preheating temperature, and accordingly, wasteful heating during a time period of reaching the sterilizing temperature is dispensed with and thermal denaturation of liquid can be restrained to a minimum.

Liquid which reaches a sterilizing temperature after having been processed during a final heating step is held for a predetermined time period as in a conventional case. It is preferable to carry out this holding step by passing liquid through a flow pass having a predetermined length. By such a holding step, sterilization becomes complete and liquid is cooled by a succeeding cooling step.

Further, according to the method of the invention, for conservation of energy, there may be provided a heat exchange step for exchanging heat of high temperature liquid after sterilization with heat of low temperature liquid before sterilization, and in this case, such heat exchange step is performed respectively during a preheating step and a cooling step. Further, according to a heat sterilization method of the invention, compared with the heat sterilization method of Prior Art 1, when a degree of heating remains the same, i.e. when F value remains the same, it is experimentally confirmed that an effect of sterilization is higher than that in the method of Prior Art 1.

According to a first mode of the invention, pressurization and release to normal pressure is performed out by a homogenizer. Whereas the low pressure homogenizer 20 in Prior Art 1 (refer to FIG. 4) is installed to homogenize liquid and can regulate pressure in a range of 2 MPa through 40 MPa, according to the first mode of the invention, it is preferable to adopt an apparatus capable of setting a higher homogenizing pressure, for example, an apparatus of a high pressure type capable of regulating homogenizing pressure within a range of from 50 MPa to 100 MPa. That is, according to a method of the invention, there is no need for using a special ultra high pressure homogenizer as in Prior Art 3, but there may be selected a high pressure type homogenizer from among homogenizers normally on sale. Accordingly, the method of the invention can be implemented inexpensively by a homogenizer on sale.

Further, different from a heating apparatus of a kind in which a rotating member is brought into contact with liquid to thereby provide frictional heat, a structure of a homogenizer is simple since there is no operating portion at a portion of the homogenizer that is in contact with liquid, which is advantageous in view of maintenance and running cost. Further, when liquid includes a fat component, by adopting a homogenizer, liquid can be heated and homogenized simultaneously. Further, when liquid includes an insoluble component of calcium or the like, a dispersion performance of such an insoluble component can be promoted. In this respect, a detailed explanation will be given later in Test Example 3.

According to a second mode of the invention, pressurization is carried out within a range of pressure from 50 MPa to 100 MPa. As mentioned above, according to a method of the invention sterilization is not carried out by operation of high pressure, but is carried out by heating. Therefore, ultra high pressure as in Prior Art 2 or 3 is not necessary. Particularly, when pressurizing is assumedly carried out at pressure exceeding 100 MPa in the method of the invention, there is a possibility of increasing power consumption of an apparatus, which is disadvantageous in view of running cost. Accordingly, pressurization is preferably carried out at 100 MPa or lower. That is, as a condition necessary for achieving operation and effect of the method of the invention with minimum power consumption, it is recommended to set pressurization within a range of from 50 MPa to 100 MPa.

According to a third mode of the invention, the operation is carried out within a range of sterilizing temperature from 90° C. to 160° C. Generally, in Prior Art 1, there is a tendency in which higher a sterilizing temperature, the more significant scorch at final heating section 35 (refer to FIG. 4). Therefore, a method of the invention can achieve a maximum effect when a sterilizing temperature is high. That is, the method of the invention is preferable when a sterilizing temperature is within a range of from 90° C. to 160° C., particularly within a range of from 120° C. to 160° C.

According to a second aspect of the invention, there is provided a continuous heat sterilization apparatus of liquid. In the following, an explanation will be given of an apparatus according to the second aspect of the invention, and to facilitate correspondence with elements of embodiments, mentioned later, as elements of the apparatus of the invention, notations of elements of embodiments are placed within parentheses. A reason for explaining the apparatus of the invention in correspondence with notations of embodiments, mentioned later, resides in facilitating understanding of the apparatus of the invention and not for limiting a technical range of the apparatus of the invention to embodiments.

Figure 2:
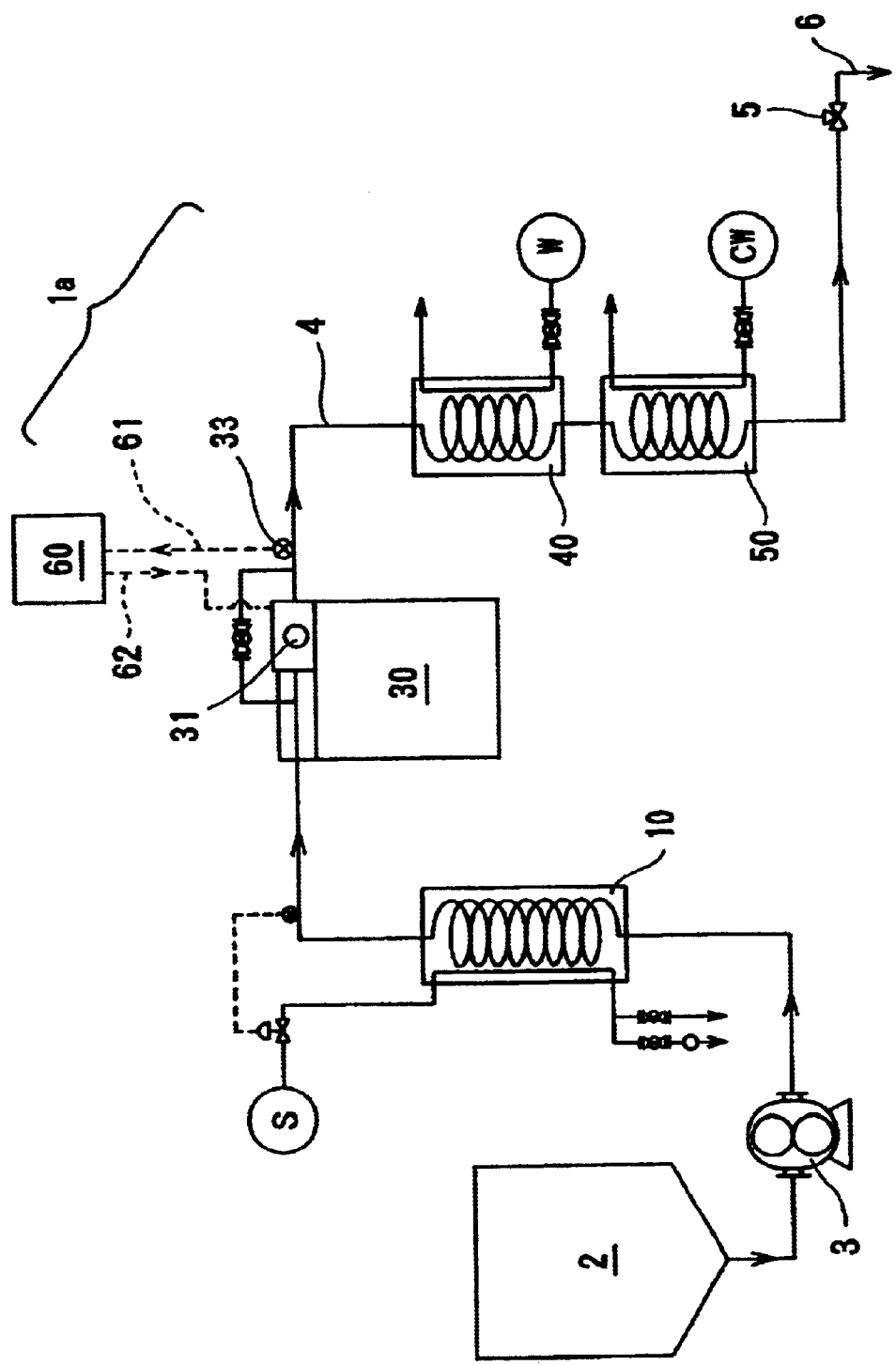
FIG. 2 is a schematic view showing another embodiment of a continuous heat sterilization apparatus for liquid according to the invention.
Figure 3:
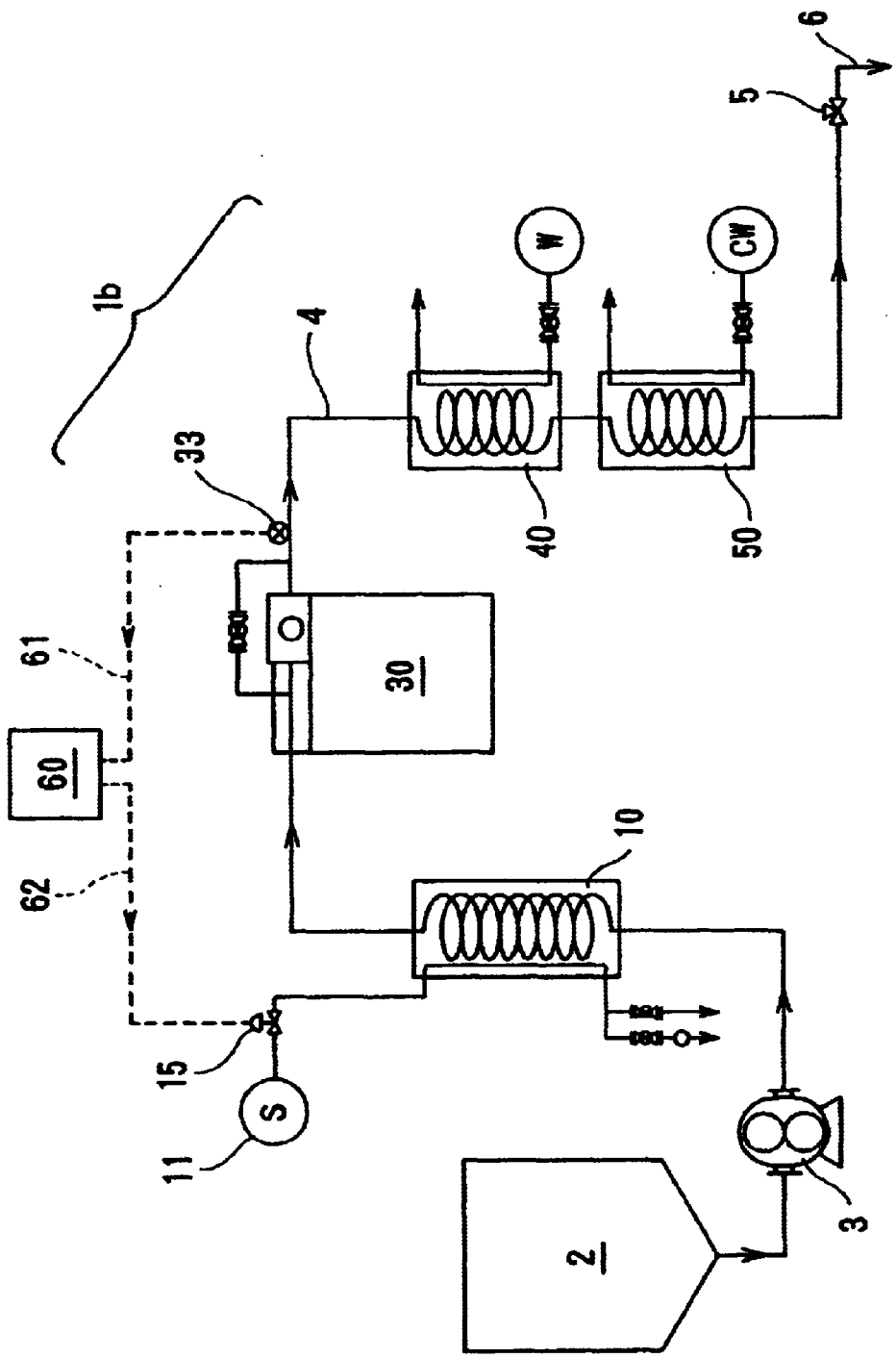
FIG. 3 is a schematic view showing still another embodiment of a continuous heat sterilization apparatus for liquid according to the invention.

FIG. 1 is a schematic view showing an embodiment of a continuous heat sterilization apparatus for liquid according to the invention, and FIG. 2 and FIG. 3 are schematic views showing other embodiments of continuous heat sterilization apparatus for liquid according to the invention, respectively.

Figure 4:
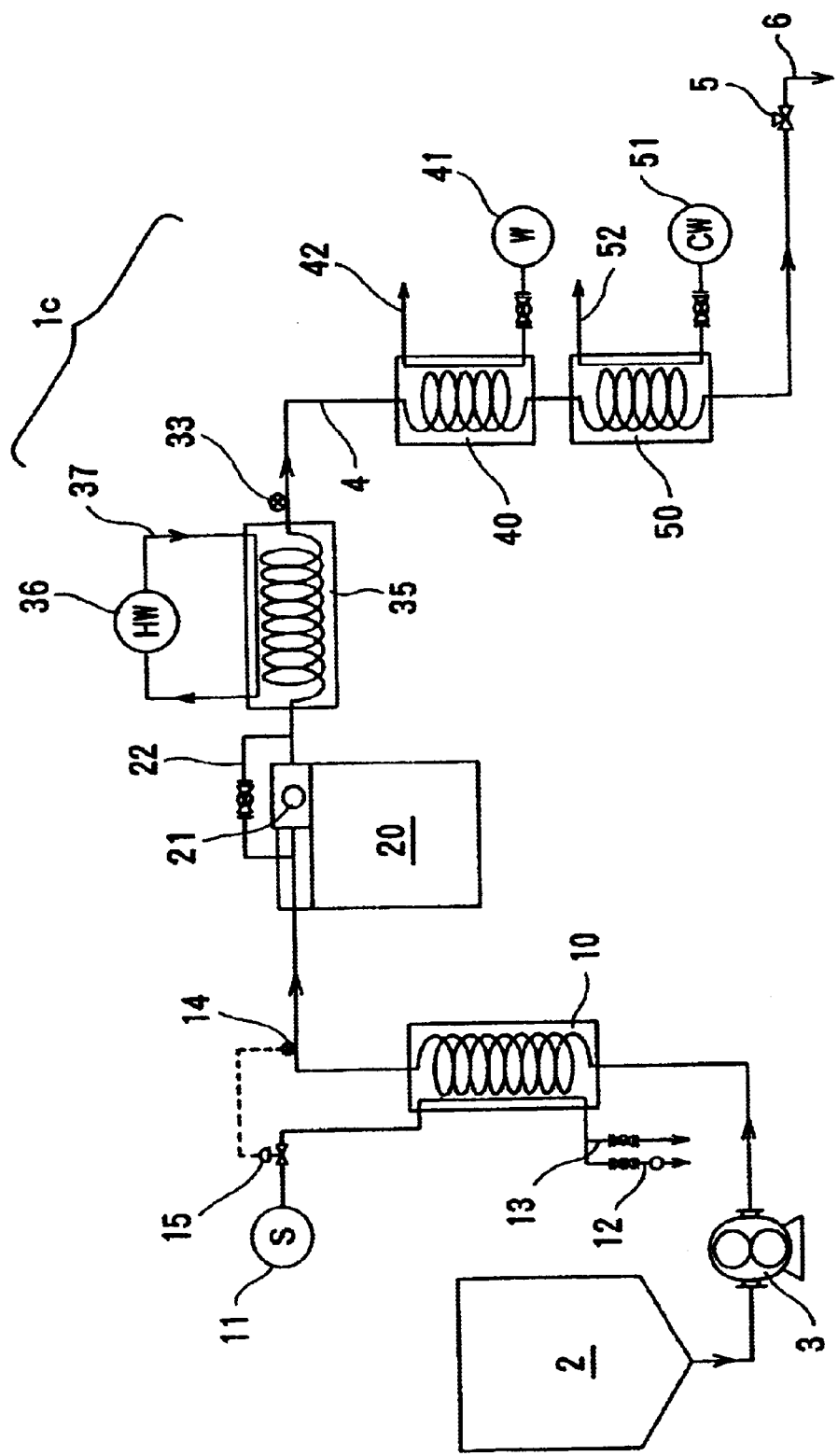
FIG. 4 is a schematic view for explaining an example of a conventional continuous heat sterilization apparatus for liquid.

A continuous heat sterilization apparatus (1, 1a, 1b) for liquid according to the invention, is provided with storage tank (2), feed pump (3), preheating section (10) and cooling sections (40 and 50), and these elements are the same as those in the apparatus of Prior Art 1 (refer to FIG. 4).

In the apparatus (1, 1a, 21b) of the invention, the feed pump (3) is provided downstream of the storage tank (2). Although a type of the feed pump (3) may be of a centrifugal type pump or a constant amount pump, when a constant amount pump is used, similar to Prior Art 1, it is preferable to install a pipe for returning liquid from an outlet pipe to an inlet pipe of the feed pump (3), and a flow regulating valve. The preheating section (10) is installed downstream of the feed pump (3).

The preheating section (10) is an apparatus for preheating liquid by heating the liquid, and various heat exchangers of a plate type, a multiple pipe type, a tube type and a scraping type may be used as the preheating section. As a heat source (11), other than steam, warm water can be used. It is preferable to install devices (14, 15) for automatically controlling temperature of liquid at an outlet of the preheating section (10), at the preheating section (10). Further, the preheating section (10) is not limited to a single one of a heat exchanger but may be of a plurality of heat exchangers for preheating liquid in steps. A pressurization release apparatus (30) is installed downstream of the preheating section (10).

The pressurization release apparatus (30) is an apparatus for continuously pressurizing preheated liquid and releasing the liquid to normal pressure within a time period of less than 10 seconds after pressurization, and is provided with, for example, a high pressure pump and a throttle valve (not illustrated). By utilization of the high pressure pump and the throttle valve, liquid is made to reach a predetermined sterilizing temperature.

It is preferable in the apparatus (1, 1a, 1b) according to the invention that as a device for making liquid reach a sterilizing temperature, a device other than the pressurization release apparatus (30) is not used along with the pressurization release apparatus, and there is installed no device for substantially heating liquid during a time period until liquid is cooled downstream of the pressurization release apparatus 30).

Generally, when a device for carrying out final heating is a device for transferring heat energy to liquid, for example, a heat exchanger, a steam blowing nozzle or the like, scorch is liable to result in this device for carrying out final heating. In contrast thereto, the apparatus of the invention only adds energy to liquid, and accordingly, almost no scorch is caused.

According to the pressurization release apparatus (30), a degree of pressurization can be changed by a small or large amount of opening a throttle valve, or an increase or a decrease in rotation of a high pressure pump. Accordingly, it is preferable that the pressurization release apparatus (30) is installed with pressure a regulating device (31) for regulating an opening amount of the throttle valve or rotation of a high pressure pump. As the pressure regulating device (31), it is particularly preferable to install a hydraulic control unit that is capable of regulating an opening amount of the throttle valve by power of hydraulic pressure.

The pressurization release apparatus (30) used in the apparatus of the invention is preferably provided with a pressurizing function of at least between 50 MPa and 100 MPa. A reason for this is that when pressurization exceeding 100 MPa is assumedly carried out, there is posed a problem in which running cost is increased since power consumption is increased. Further, liquid flowing in the pressurization release apparatus (30) is liquid before sterilization. Accordingly, there is no need to adopt a high pressure pump for sterilization, as in the case in which low pressure homogenizer 20 (refer to FIG. 4) is installed downstream of final heating section 35, and a homogenizer as specified is normally sufficient. Also in this regard, according to the apparatus of the invention, an investment cost and running cost become low.

The Holding pipe (4) is installed downstream of the pressurization release apparatus (30). The holding pipe (4) is a pipe pass reaching the cooling sections (40 and 50) from the pressurization release apparatus (30). A time period of holding liquid can be regulated to be long or short according to a length of the holding pipe (4) and a flow rate of liquid. Length of the holding pipe (4) can pertinently be determined.

It is preferable to surround the pressurization release apparatus (30) and/or the holding pipe (4), mentioned above, by an insulating member in order to restrain heat loss caused by radiating heat as much as possible. Further, there may be carried out an operation of compensating for heat loss by installing an electric heater or the like at an underlayer of the insulating member. Accordingly, when the apparatus (1, 1a, 1b) is started up, a thermally stable state can swiftly be reached.

The cooling sections (40 and 50) may be of any type as long as they can cool liquid, and various heat exchangers of a plate type, a multiple pipe type, a tube type and a scraping type can be used as the cooling sections. Further, the cooling sections (40 and 50) are not limited to single ones of heat exchangers, but may be pluralities of heat exchangers for cooling liquid in steps.

Further, although the apparatus (1, 1a, 1b) of the invention may be installed with a heat exchange section (not illustrated) for exchanging heat of high temperature liquid after sterilization and heat of low temperature liquid before sterilization, this heat exchange section can be regarded as portions of the preheating section (10) and the cooling sections (40 and 50).

According to the apparatus (1, 1a, 1b) of the invention mentioned above, a heat conductive wall or steam nozzle of a heat exchanger is not scorched as in Prior Art 1, and accordingly, efficiency of heat transfer is not deteriorated with elapse of time and a long time period of continuous operation is feasible. Further, in the pressurization release apparatus (30), temperature is elevated substantially instantaneously, and accordingly, wasteful heating during a time period until reaching a sterilization temperature is dispensed with, and as a result, heat denaturation of liquid is insignificant.

According to a fourth and a fifth mode of the invention, there are provided apparatus in which the continuous heating sterilizing apparatus (1, 1a, 1b) of the invention is arranged with an automatic controlling device (15, 31, 33 and 60 through 62).

According to the fourth mode of the invention, there are installed a temperature sensor (33) and controlling device (60). The temperature sensor (33) is installed at holding pipe (4) for detecting temperature of liquid coming out from pressurization release apparatus (30). Although any kind of temperature sensor, such as a thermoelectric thermometer or a resistance thermometer, may be used as temperature sensor (33), it is necessary that temperature can be detected electrically. The controlling device (60) is a device for comparing a detection value detected by the temperature sensor (33) with a previously inputted target value of a sterilizing temperature and calculating an amount of operation toward a direction in which both coincide with each other. Pressure regulating device (31) is a device for regulating temperature of liquid coming out from the pressurization release apparatus (30) by increasing or decreasing a degree of pressurization of the pressurization release apparatus (30) in accordance with an amount of operation calculated by the controlling device (60). Although as an example of the pressure regulating device (31), an invertor for adjusting rotational amount of the high pressure pump can be exemplified, it is preferable to use a hydraulic pressure control unit for regulating an opening amount of a throttle valve (not illustrated).

In this way, by increasing or decreasing degree of pressurization in the pressurization release apparatus (30), temperature at an outlet of the pressurization release apparatus (30) can automatically be controlled to a previously inputted and set target value (that is, predetermined sterilizing temperature).

According to a fifth mode of the invention, there is provided an apparatus for regulating temperature of liquid on an output side of the pressurization release apparatus (30), and automatically controlling the temperature to a predetermined sterilizing temperature by increasing or decreasing temperature of liquid on an inlet side of the pressurization release apparatus (30). That is, according to the fifth mode, there are provided temperature sensor (33) and controlling device (60) similar to the fourth mode, and also a device (15) for regulating temperature at an inlet of the pressurization release apparatus as well. As an example of a device for regulating an inlet temperature of the pressurization release apparatus, for example, when an inlet temperature of the pressurization release apparatus (30) is determined by preheating section (10), an apparatus for regulating an amount of heating in the preheating section (10) can be used. Particularly.,when the preheating section (10) is a heat exchanger for heating liquid by steam, a steam regulating valve for regulating an amount of steam can be used. In this case, an amount of operation calculated by the controlling device (60) is outputted to steam regulating valve. That is, the controlling device (60) determines an opening amount of the steam regulating valve to thereby increase or decrease an amount of heating liquid in the preheating section (10) to thereby increase or decrease temperature on the inlet side of the pressurization release apparatus (30). By increasing or decreasing temperature on the inlet side of the pressurization release apparatus (30), temperature on the outlet side of the pressurization release apparatus is automatically controlled to a predetermined sterilizing temperature.

There may be installed a local automatic control device (not illustrated) for controlling an amount of pressurization in the pressurization release apparatus (30) according to the fourth mode, or for controlling temperature on the inlet side of the pressurization release apparatus (30) according to the fifth mode, to a respective predetermined target value. In this case, there may be constituted control of a cascade type in which the controlling device (60) outputs a target value to the local automatic control device. That is, the controlling device (60) may be constituted separately to respective functions or may be constituted integrally. For example, the local automatic control device and the controlling device (60) may be summarized as the controlling device (60) of the apparatus of the invention. Further, both of the fourth mode and the fifth mode can be used.

According to a sixth mode of the invention, there is provided an apparatus featured in that pressurization release apparatus (30) is a homogenizer. As described in the explanation of Prior Art 1, generally, the homogenizer is installed with a high pressure pump and a homogenizing valve, and according to the sixth mode the homogenizing valve is a throttle valve according to the invention, mentioned above, and a homogenizing pressure is an "amount of pressurization of the pressurization release apparatus". According to the homogenizer, it is preferable to adopt an apparatus of a high pressure type capable of regulating a homogenizing pressure within, for example, a range of from 50 to MPa to 100 MPa. Further, when liquid includes a fat component, although the homogenizer achieves an operation of homogenizing liquid, and accordingly, as a principle, another homogenizing apparatus needs not to be installed, one may be installed.

Although any liquid may be treated by a continuous heat sterilization method and apparatus according to the invention as mentioned above, a case in which liquid is food, drug or raw materials of these is particularly preferable since an effect of the invention can most assuredly be achieved. Further, as specific food to be treated, other than liquid having a comparatively low viscosity such as water, milk, juice or wine, the liquid may be of a high viscosity such as a paste-like food, and the invention is applicable thereto so long as the liquid can be flowed at least in a pipe pass.

Next, a detailed explanation will be given of the invention by showing Tests.

TEST 1

This test is carried out for confirming an effect of heat sterilization according to the invention.

TEST APPARATUS

A test apparatus is fabricated based on FIG. 1 (refer to Example 1 mentioned later). That is, in FIG. 1, a small-sized tank (capacity: 7 liter) is adopted as storage tank 2, a feed pump (made by Yasuda Fainte Co. Ltd., 30 l/h type) is adopted as feed pump 3, as preheating section 10 and first cooling section 40 and second cooling section 50, small-sized tube type heat exchangers are respectively adopted, and as pressurization release apparatus 30 a high pressure homogenizer (made by APV Co. Ltd., 8-30 type) is adopted. These devices are connected to each other by small-diameter pipes having an inner diameter of 4 mm in accordance with FIG. 1 to thereby constitute the test apparatus.

PREPARATION OF SAMPLE

Unsterilized milk of 7 liters at 10° C. is received in the storage tank 2, transmitted to the preheating section 10 by a supply amount of 8 l/h by the feed pump 3, sterilized by regulating an inlet pressure of the pressurization release apparatus 30 to 0.3 MPa and an outlet pressure of the high pressure homogenizer to 0.5 MPa, and cooled to about 5° C. via the first cooling section 40 and the second cooling section 50. During this treatment, a preheating temperature is changed in steps within a range of 110 to 130° C., a homogenizing pressure is changed in steps within a range of from 50 to 100 MPa, and a sterilizing temperature is changed in steps within a range of from 135 to 50° C. to thereby prepare samples 1 through 7 in accordance with various sterilizing conditions shown by Table 1.

Further, control sample 1, which is the same as the above-described unsterilized milk, is sterilized under a condition of 140° C. and 2 seconds by a normal plate-type sterilizer (made by Morinaga Engineering Co. Ltd., MAU 200 l/h type, refer to FIG. 4), and cooled. Control sample 2 is similarly sterilized under a condition of 150° C. and 2 seconds by a direct steam blowing type sterilizer (made by Morinaga Engineering Co. Ltd., MDU 200 l/h type) and cooled.

COMPARISON OF EFFECT OF STERILIZATION, DENATURATION DEGREE OF PROTEIN, AND FLAVOR (a) Effect of Sterilization With respect to samples 1 through 7 and control samples 1 and 2, bacteria count is measured by a standard flat plate incubation method ("Six Food and Hygiene Laws, edition of Heisei 7 (1995)" supervised by Welfare Ministry, Life and Hygiene Bureau, pages 133–135, August 25, Heisei 6 (1994)), and sterilization performance is confirmed by a bacteria test ("Six Food and Hygiene Laws, edition of Heisei 7 (1995)" supervised by Welfare Ministry, Life and Hygiene Bureau, page 581, August 25, Heisei 6 (1994)).

(b) Denaturation Degree of Protein

With respect to samples 1 through 7 and control samples 1 and 2, nitrogen in protein of milk serum is measured by the following method to thereby constitute an index of a degree of denaturation of protein.

Each sample is supplied to a centrifugally precipitating pipe of 50 ml, provided with sodium chloride, salted out and filtered. A filtered solution is provided with acetic acid, turbidity is measured by an absorption degree at 420 nm by using a spectrophotometer (made by Hitachi Seisakusho Co. Ltd., U-2000 type double beam), and nitrogen in protein of milk serum is calculated from an analytic curve.

(c) Flavor

By panelists of 20 persons of males and females, a flavor test of respective samples was carried out, evaluation was carried out for the following four stages, and average values of respective samples were calculated.

No heating smell and raw taste: +2 points
Less heating smell and raw taste: +1
point Heating smell and rather failed: −1
Failed: −2 points (4) Results Test results are shown by Table 1. In Table 1, "−" in the column of "bacteria test", (a2) is a notation indicating negative.

As is apparent from Table 1, bacteria count is 0 and a result of bacteria test is negative for all the samples. Further, with respect to point of flavor, samples 1 through 7 are generally excellent as compared with control samples 1 and 2, and particularly, extremely excellent results are obtained for samples 1 through 3. Further, with respect to denaturation degree of protein, a degree of denaturation is small in samples 1 through 3 which agrees with results of the point of flavor.

As a result, it is recognized that the continuous heating method and apparatus of the invention can sterilize liquid safely and assuredly as compared with conventional methods. Further, it is found that a denaturation caused by heat for liquid is insignificant. Further, although similar tests are carried out by variously changing the kind of liquid, a sterilizing temperature and a holding time, a homogenizing pressure and a preheating temperature, substantially similar results are obtained.

TABLE 1

| Samples | Sterilizing condition (Annotation 1) | | | | Result (Annotation 2) | | | |
| --- | --- | --- | --- | --- | --- | --- | --- | --- |
| | I | II | III | IV | a1 | a2 | b | c |
| Sample 1 | 110 | 100 | 135 | 2.0 | 0 | — | 4.2 | +2.0 |
| Sample 2 | 115 | 100 | 140 | 1.5 | 0 | — | 3.8 | +1.8 |
| Sample 3 | 120 | 80 | 140 | 2.0 | 0 | — | 3.3 | +1.7 |
| Sample 4 | 120 | 100 | 145 | 0.7 | 0 | — | 3.2 | +1.5 |
| Sample 5 | 128 | 70 | 145 | 1.0 | 0 | — | 2.9 | +1.3 |
| Sample 6 | 125 | 100 | 150 | 0.3 | 0 | — | 2.7 | +1.0 |
| Sample 7 | 138 | 50 | 150 | 0.5 | 0 | — | 2.4 | +0.7 |
| Control sample 1 | 110 | | 140 | 2.0 | 0 | — | 2.9 | −0.5 |
| Control sample 2 | 80 | | 150 | 2.0 | 0 | — | 2.0 | −1.5 |

Annotation 1) I: Preheating temperature (° C.), II: Pressure (MPa), III: Sterilizing temperature (° C.), IV: Holding time (second)
Annotation 2) a1: Bacteria count, a2: Bacteria test, b: Denaturation degree (mg/g), c: Point of flavor

TEST 2

This test is carried out for comparing quality of a product (milk green tea drink), sterilized by the heat sterilization method according to the invention and a conventional plate-type sterilizing method.

(1) Test Apparatus

A test apparatus is fabricated based on FIG. 1 (refer to Example 1, mentioned later). That is, in FIG. 1, a tank (capacity; 130 liter) is adopted as storage tank 2, a feed pump (made by Yasuda Fainte Co. Ltd., 200 l/h) adopted as feed pump 3, as preheating section 10 and first cooling section 40 and second cooling section 50, plate-like heat exchangers are respectively adopted, and as pressurization release apparatus 30 a high pressure homogenizer (made by APV Co. Ltd., Ranniel 2-51H) is adopted. These devices are connected by pipes having an inner diameter of 8 mm in accordance with FIG. 1 to thereby constitute the test apparatus.

(2) Preparation of Sample 100 kg of milk green tea drink is obtained by mixing 6.0 kg of skim milk, 0.7 kg of non-salt butter, 6.0 kg of liquid sugar, 0.5 kg of green tea and 0.3 kg of a stabilizer in 86.5 kg of dissolving water. A 100 kg sample of the milk green tea drink is held at 10° C. in the storage tank 2 (refer to FIG. 1) of the test apparatus, transmitted to the preheating section 10 by a supply amount of 200 l/h by the feed pump 3, and sterilized in the pressurization release apparatus 30 by setting an inlet temperature to 120° C., an inlet pressure to 0.4 MPa, an outlet pressure to 0.7 MPa, a homogenizing pressure to 90 MPa, temperature on an outlet side of the pressurization release apparatus (sterilizing temperature) to 140° C. and a holding time to 2 seconds. Further, the sample is cooled to 5° C. via the first cooling section 40 and the second cooling section 50 to thereby prepare a test sample. In the meantime, the milk green tea drink of the same composition is sterilized by a conventional plate-type sterilizer (made by Morinaga Engineering Co. Ltd., MAU 200 l/h type, refer to FIG. 4) at 140° C. for 2 seconds, and is cooled to thereby prepare a control sample.

(3) Procedures (a) Sterilization Effect

With respect to the test samples and the control sample, bacteria count is measured by a standard flat plate incubation method the same as in Test 1, sterilization performance is confirmed by a bacteria test the same as in Test 1, the test sample and the control sample are preserved in a constant temperature chamber at 37° C. for 5 days, and thereafter, measurement of bacteria count and bacteria test are carried out similarly.

(b) Outlook

The test sample and the control sample are preserved in cold and chromaticity is measured by using a color difference meter (made by Nippon Denshoku Kogyo Co. Ltd. SZ-Σ80) with respect to the two preserved samples.

(c) Flavor

By panelists of 15 persons of males and females, flavors of the test sample and the control sample are compared to evaluate each sample with respect to the following three items.

Item 1: Which is stronger in smell of green tea?

Item 2: Which is less in heating smell?

Item 3: Which is more delicious?

Results of a number of panelists, who evaluated one higher than the other with regard to the test sample and the control sample, are summed up. Further, a panelist who answers "neither" is excluded in summing up the results.

(4) Results

The results are as follows.

(a) Sterilization Effect

With respect to sterilization effect, bacteria count is 0 for both of the samples, and results of the bacteria test are also negative. Further, these results remain the same even after preserving the samples in the constant temperature chamber at 37° C. for 5 days. Accordingly, the sterilization effect is sufficient for either of the sterilization methods.

(b) Outlook

Figure 5A:
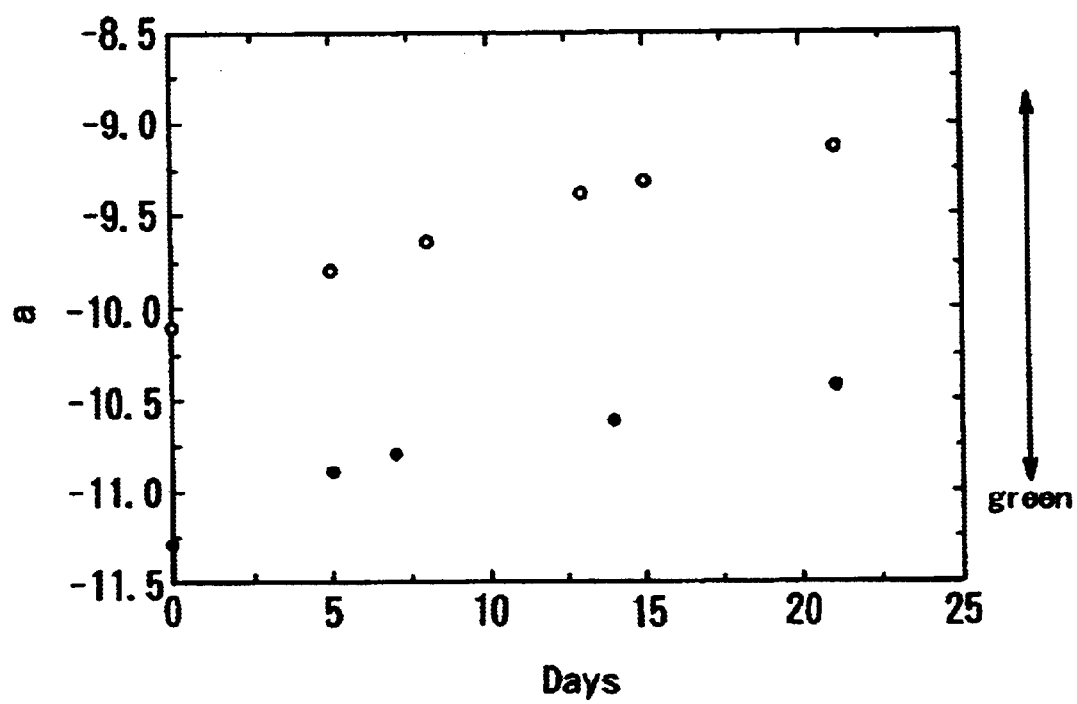
FIGS. 5A and 5B are graphs indicating results of measuring chromaticity during a time period in which a sample of Test Example 2 and a control sample are preserved.
Figure 5B:
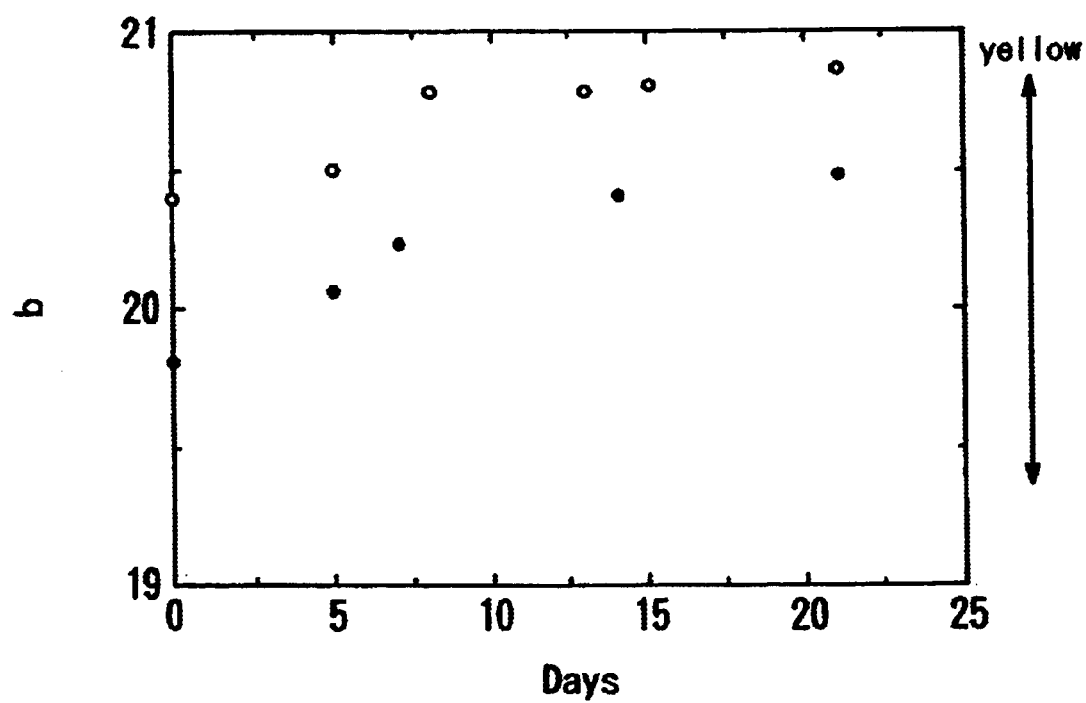

Test results of outlook are shown by FIG. 5(A) and FIG. 5(B). FIGS. 5(A) and 5(B) show graphs indicating test results of chromaticity during a time period of preserving the test sample and the control sample of Test 2. FIG. 5A is a graph indicating a measurement result of a value of "a" of color difference designated by a color system of L*a*b*, and FIG. 5B is a graph showing a test result of a value of "b" of color difference designated by the color system of L*a*b*. In FIG. 5A, the ordinate shows the value of "a" and the abscissa shows a number of elapsed days for preserving both samples. Further, in FIG. 5B, the ordinate shows the value of "b" and the abscissa shows a number of elapsed days of preserving both samples. In FIGS. 5A and 5B, (•) shows a measurement result of the test sample and (0) shows a measurement result of the control sample. Further, these graphs signify that the smaller the value of "a" the stronger a color tone of green and the larger the value of "b" the stronger a color tone of yellow. Accordingly, FIG. 5(A) signifies that the smaller the value of "a" the darker a color of tea, and FIG. 5(B) signifies that the larger the value of "b" the more significant a change of a color to brown.

It is apparent from FIG. 5A that the value of "a" is smaller in the test sample (•) rather than it is for the control sample (0), and thus the color of tea is darker for the test sample. Further, it is apparent from FIG. 5B that the value of "b" is smaller for the test sample (•) than it is for the control sample (0), and thus the change of color to brown is smaller for the test sample. As a result, it becomes apparent that with respect to outlook, the test sample is more excellent than the control sample.

(c) Flavor

Test results of flavor are shown by Table 2. As is apparent from Table 2, a number of panelists determines that the test sample is superior to the control sample with respect to all of items 1 through 3. As a result of Test 2, it is found that compared with a product sterilized by a conventional method, a product sterilized by the method of the invention is excellent in both of outlook and flavor although sterilizing effects of these methods are equivalent to each other.

TABLE 2

| Flavor item | No. of panelists evaluated to be superior | |
|---|---|---|
| | Test sample | Control sample |
| Item 1 | 25 | 2 |
| Item 2 | 12 | 2 |
| Item 3 | 28 | 2 |

TEST 3

This test is carried out for comparing qualities of products (calcium enriched milk) sterilized by the heat sterilization method according to the invention and a conventional plate-type sterilizing method.

(1) Test Apparatus

A test apparatus the same as that of Test 2 is used.

(2) Preparation of Sample 10.4 kg of skim milk, 2.4 kg of non-salt butter and 0.2 kg of milk calcium are dissolved in 87.0 kg of dissolving water and cooled to thereby prepare 100 kg of unsterilized calcium enriched milk. The calcium enriched milk is put into storage tank 2, transmitted to preheating section 10 by a supply amount of 200 l/h by feed pump 3, sterilized by regulating an inlet temperature of pressurization release apparatus 30 to 110° C., an inlet pressure thereof to 0.4 MPa and an outlet pressure thereof to 0.7 MPa, and is cooled to 5° C. via first cooling section 40 and second cooling section 50. During this occasion, a homogenizing pressure is set to 90 MPa, a temperature (sterilizing temperature) on an output side of the pressurization release apparatus and a holding time are set to 130° C. and 2 seconds, respectively. The cooled sterilized calcium enriched milk is filled into a milk bottle to thereby prepare a test sample.

In the meantime, unsterilized calcium enriched milk of the same composition is sterilized under conditions of 130° C. and 2 seconds by a normal method by using a test apparatus of a conventional plate-type sterilizer (treating capacity; 200 l/h, made by Morinaga Engineering Co. Ltd.), and cooled to thereby prepare sterilized calcium enriched milk. This sterilized calcium enriched milk is filled into a milk bottle to thereby prepare a control sample.

(3) Procedures

The test sample and the control sample are left stationarily in a refrigerator, and following respective items (a)–(d) are test on a day of sterilization, and the third day and the seventh day after sterilization.
(a) Floating Up of Fat to an Upper Portion of Calcium Enriched Milk With respect to the test sample and the control sample, states at upper portions of calcium enriched milk in the milk bottles are observed by naked eyes, and whether fat is floated up in the milk confirmed.
(b) Presence or Absence of Precipitated Matters at Bottom Portions of Milk Bottless With respect to the test sample and the control sample, the calcium enriched milks are stationarily flowed out from the milk bottles, and whether precipitated matter is generated at the bottom portions of the milk bottles is confirmed by naked eyes.
(c) Adherence of Solid Matters to Side Wall Portions of Milk Bottles During observation of the above item (b), whether solid matter adhered to side wall portions of the milk bottles is confirmed simultaneously by naked eyes.
(d) Calcium Concentration The calcium enriched milk is sampled at a position of the milk bottles 40 mm below liquid levels, and calcium concentration is measured by a calcium magnesium counter (made by Hiranuma Sangyo Co. Ltd., CM-212).

(4) Results

Results are as follows.
(a) Floating up of Fat to Upper Portion of Calcium Enriched Milk Test results with regard to floating up of fat is shown by Table 3. Table 3 is a table indicating a result of observation by naked eyes with regard to whether fat is generated at an upper portion of the milk bottles with respect to the test sample and the control sample. In Table 3, notations designate as follows.

–: No confirmation

±: Confirmation of small amount

+: Confirmation of clear amount

++: Confirmation of much amount

Further, significances of notation remain same in Table 4 and Table 5, mentioned later.

As is apparent from Table 3, with respect to the test sample, fat is not floated up to the upper portion in the milk bottle during any of the day of sterilization, the third day after sterilization and the seventh day after sterilization; however, with respect to the control sample, floating up of fat is clearly observed on the third day after sterilization, and a large amount of fat is floated up on the seventh day after sterilization. It is apparent from these results that a state of dispersing fat particles in calcium enriched milk sterilized by the method of the invention is more excellent than that using conventional technology.

TABLE 3

| No. of elapsed days | Observation result | |
|---|---|---|
| | Test sample | Control sample |
| Day of sterilization | – | ± |
| After 3 days | – | + |
| After 7 days | – | ++ |

(b) Presence or Absence of Precipitated Matters at Bottom Portions of Milk Bottles Test results concerning precipitated matter is as shown by Table 4. Table 4 is a table showing a result of observing presence or absence of precipitated matter at bottom portions of the milk bottles with regard to the milk bottles of the test sample and the control sample. As is apparent from Table 4, with regard to generation of precipitated matter at the bottom portions of the milk bottles, according to the test sample no precipitated matter is generated on the day of sterilization, a small amount of precipitated matter is generated on the third day after sterilization, and generation of precipitated matter becomes apparent on the seventh day after sterilization, whereas according to the control sample, generation of precipitated matter becomes apparent on the third day after sterilization and a large amount of precipitated matter is generated on the seventh day after sterilization.

Further, when precipitated matters generated in the test sample is shaken by hand by injecting water into the milk bottle, the precipitated matters is dispersed simply into water. However, when precipitated matter generated in the control sample is similarly shaken, almost no precipitated matter is dispersed.

It becomes apparent from these results that a state of dispersing calcium in calcium enriched milk sterilized by the method of the invention is more excellent than that using conventional technology and redispersion of precipitated matter is easy.

TABLE 4

| No. of elapsed days | Observation result | |
|---|---|---|
| | Test sample | Control sample |
| Day of sterilization | – | ± |
| After 3 days | ± | + |
| After 7 days | + | ++ |

(c) Adherence of Solid Matters to Side Wall Portions of Milk Bottles

Test results with regard to solid matter at the side wall portions of the milk bottles is shown by Table 5. Table 5 is a table showing a result of observing whether solid matter is adhered to side wall portions with respect to the milk bottles of the test sample and the control sample.

As is apparent from Table 5, according to the test sample, no adherence of solid matter to the side wall portion of the milk bottle is recognized in any of the day of sterilization, the third day after sterilization and the seventh day after sterilization, whereas according to the control sample, adherence of a large amount of solid matter to the side wall portion of the milk bottle is recognized on the day of sterilization, and the third and seventh day thereafter. It becomes further apparent from these results that a state of dispersing calcium of calcium enriched milk sterilized by the method of the invention is more excellent than that using conventional technology.

TABLE 5

| No. of elapsed days | Observation result | |
| --- | --- | --- |
| | Test sample | Control sample |
| Day of sterilization | − | ++ |
| After 3 days | − | ++ |
| After 7 days | − | ++ |

(d) Calcium Concentration

Figure 6:
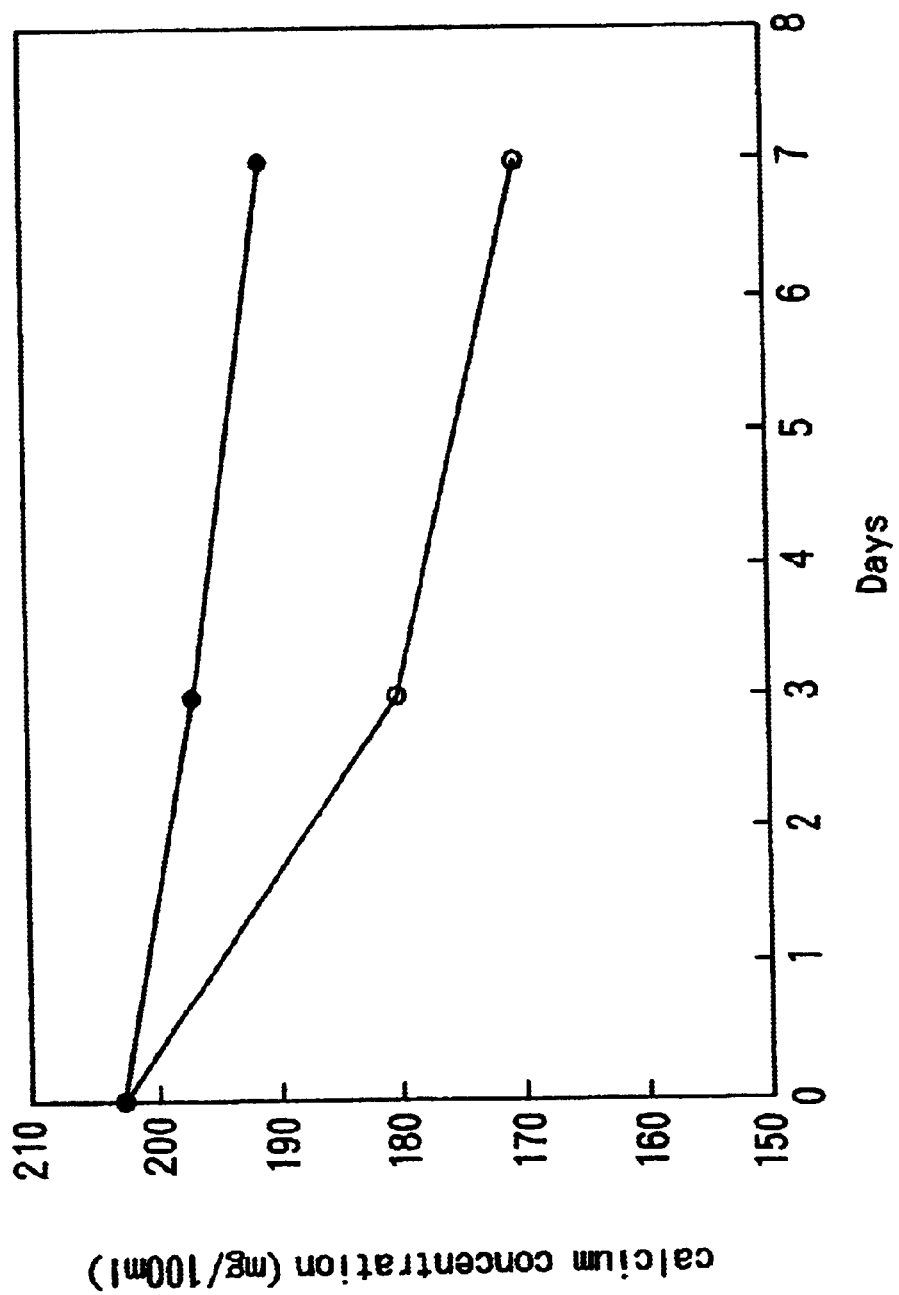
FIG. 6 illustrates graphs showing time-sequential changes in calcium concentration at upper portions of milk bottles during a time period in which a test sample of Test Example 3 and a control sample are preserved.

Test results with regard to calcium concentration is shown by FIG. 6. FIG. 6 illustrates graphs showing time-sequential changes of calcium concentrations at upper portions in the milk bottles during a time period in which the test sample and the control sample are preserved. In FIG. 6, the abscissa designates a number of elapsed days (day), the ordinate designates calcium concentration (mg/100 ml). Also, in FIG. 6 • designates the test sample and 0 designates the control sample.

It is apparent from FIG. 6 that compared with the control sample, concentration of calcium in the test sample is stabilized and precipitation of calcium is small.

It is found from respective results mentioned above that when the invention is applied to sterilization of calcium enriched milk, as compared with sterilization using conventional technology, floating up of fat of the sterilized calcium enriched milk, precipitation of solid matter at the bottom portion of the milk bottle and adherence of solid matter to the side wall portion of the milk bottle are small, and the state of dispersing fat particles and calcium is generally excellent. Further, it is found that a reduction in calcium concentration at the upper portion of the milk bottle is small and precipitation of calcium is insignificant.

It is found from the results of the tests, as compared with using conventional sterilizing technology, that the method of the invention is particularly preferable when liquid including an insoluble component of calcium or the like is sterilized.

Next, a detailed explanation will be given of the invention by showing Examples; however, the invention is not limited to the following Examples.

EXAMPLE 1

FIG. 1 is a schematic view showing an embodiment of the apparatus for continuous heat sterilization of liquid according to the invention. In FIG. 1, elements the same as those in FIG. 4 are attached with notations the same as those in FIG. 4, and a detailed explanation of these elements will be omitted.

In FIG. 1, continuous heat sterilization apparatus 1 according to the invention includes storage tank 2 (made of stainless steel, 20 t type), feed pump 3 (made by Yasuda Fainte Co. Ltd., gear type), preheating section 10, first cooling section 40 and second cooling section 50 (both of which cooling sections are plate-type heat exchangers, made by Morinaga Engineering Co. Ltd.). Although an outlet portion of the storage tank 2 is connected with a water supply port for performing a water operation, illustration thereof is omitted in FIG. 1. On a downstream side of the preheating section 10, there is provided high pressure homogenizer or pressurization release apparatus 30 (made by APV Co. Ltd., 45.175H type, treating capacity; 8 t/h, homogenizing pressure regulating range; 5–100 MPa). Although the high pressure homogenizer 30 is provided with the hydraulic pressure control unit 31 and a bypass pipe 32, functions of these elements are the same as those of hydraulic pressure control unit 21 and bypass pipe 22 in FIG. 4. The downstream side of the high pressure homogenizer 30 is also provided with the first cooling section 40 and the second cooling section 50 via the holding pipe 4. A downstream side of the second cooling section 50 is provided with back pressure regulating valve 5 and reaches sterilized liquid outlet 6. Further, although in the continuous heat sterilization apparatus 1 of FIG. 1, there are installed pipes and devices for initially sterilizing pipe passes during a prestage of sterilizing liquid, as well as pipes and devices for cleaning the pipe passes after sterilizing liquid, illustration thereof is omitted. Further, although there are installed various pressure meters and thermometers for optically recognizing pressures or liquid temperatures in pipes and devices for automatically controlling pressures and temperatures at respective locations, illustration thereof is omitted.

Next, an explanation will be given of operation of the continuous heat sterilization apparatus 1 shown by FIG. 1. Liquid stored in the storage tank 2 is transmitted to the preheating section 10 by the feed pump 3. In the preheating section 10, liquid is preheated to a predetermined preheating temperature and is transmitted to the high pressure homogenizer 30. Although, similar to Prior Art 1, the feed pump 3 is provided with a pipe for returning liquid from an outlet pipe to an inlet pipe, and a flow rate regulating valve, illustration thereof is omitted in FIG. 1. By the pipes and the flow rate regulating valve, not illustrated, the feed pump 3 is provided with a function of elevating pressure in a pipe pass to the high pressure homogenizer 30, and inner pressure of a pipe on an inlet side of the high pressure homogenizer 30 (inlet pressure) can freely be set.

Liquid flowed into the high pressure homogenizer 30 is immediately pressurized and successively released to normal pressure via a homogenizing valve (not illustrated). A time period from pressurization to release is about 2 seconds. Further, during a procedure of the pressurization and release, mechanical energy of the high pressure homogenizer 30 is converted into heat energy, liquid is heated, and a predetermined sterilizing temperature is reached.

Liquid is held by passing through the holding pipe 4, cooled by the first cooling section 40 and the second cooling section 50, and is transmitted 15 from the sterilized liquid outlet 6 to a succeeding step via the back pressure regulating valve 5. Further, by the back pressure regulating valve 5, an inner pressure of a pipe on an outlet side of the high pressure homogenizer 30 (outlet pressure) can be regulated.

EXAMPLE 2

An explanation will be given of an example of a method for continuous heat sterilization of milk using the continuous heat sterilization apparatus 1 according to Example 1.

In the continuous heat sterilization apparatus 1 of Example 1, hot water is circulated through all of pipe passes from an outlet of the storage tank 2 to the sterilized liquid outlet 6 to thereby sterilize insides of the pipe passes. Thereafter, water is introduced from an outlet portion of the storage tank 2 into the pipe passes, and a water operation is carried out until all pipes are thermally stabilized. 20 t of unsterilized milk at 10° C. is stored in the storage tank 2, then the unsterilized milk is flowed from the storage tank 2 and sterilization is started. The unsterilized milk is press-fed to the preheating section 10 by the feed pump 3, and an outlet temperature of the preheating section 10 is regulated and automatically controlled to 115° C. by using temperature sensor 14 and steam regulating valve 15. During this occasion, a delivery pressure of the feed pump 3 is regulated and an inlet pressure of the high pressure homogenizer 30 is set to 0.3 MPa.

In the high pressure homogenizer 30, the homogenizing valve is adjusted by hydraulic pressure by using the hydraulic pressure control unit 31, a homogenizing pressure is regulated to 100 MPa, and temperature of milk on an outlet side of the high pressure homogenizer 30 is set to 140° C. During this occasion, the back pressure regulating valve 5 is regulated and an outlet pressure of the high pressure homogenizer 30 is maintained at 0.5 MPa. A time period of flowing liquid, after coming out from the high pressure homogenizer 30 and reaching the cooling section 40 is calculated from a length of the holding pipe 4 and a flow rate of milk to be 2 seconds.

Tap water at 20° C. is flowed to the first cooling section 40 and chilled water at 3° C. is flowed to the second cooling section 50, whereby sterilized milk is cooled to 5° C. and finally 19.9 t of sterilized milk is provided.

With respect to the sterilized milk, as a result of observing fat balls by an optical microscope, it is confirmed that fat particles are fine and sufficiently homogenized. Further, although bacteria count is measured similar to Test 1, bacteria is not detected.

EXAMPLE 3

An explanation will be given of a method for continuous heat sterilization of milk coffee drink by using the continuous heat sterilization apparatus 1 according to Example 1.

(1) Preparation of Milk Coffee Drink 4500 kg of a milk component solution is produced by mixing 420 kg of 10 skim milk, 180 kg of non-salt butter, 280 kg of liquid sugar and 20 kg of a stabilizer by adding these ingredients to 3600 kg of dissolving water. The produced milk component solution is mixed with 500 kg of a coffee extracted solution, extracted separately, to thereby prepare 5000 kg of a milk coffee drink.

(2) Heating and Sterilizing 5000 kg of the milk coffee drink at 10° C. is put into the storage tank 2 and sterilization of the milk coffee drink is carried out by a procedure similar to that of Example 2.

4900 kg of the sterilized milk coffee drink is prepared under conditions of a preheating temperature of 110° C., an inlet pressure of the high pressure homogenizer 30 of 0.3 MPa, a homogenizing pressure of the high pressure homogenizer 30 of 100 Mpa, a sterilizing temperature of 135° C., an outlet pressure of the high pressure homogenizer of 0.5 MPa, and a post-cooling temperature of 5° C.

With respect to the sterilized milk coffee drink, when fat particles are observed similar to Embodiment 2, it is confirmed that the sterilized milk coffee drink is sufficiently homogenized, and although measurement of bacteria count is carried out similar to Test 1, bacteria is not detected.

EXAMPLE 4

An explanation will be given of another example (embodiment of per os liquid food) of a continuous heat sterilization method using the continuous heat sterilization apparatus 1 according to Example 1.

(1) Preparation of Per Os Liquid Food 10 t of per os liquid food is provided by adding and mixing 500 kg of casein sodium, 200 kg of soybean oil, 1200 kg of dextrin, 25 kg of a stabilizer on sale, 10 kg of an emulsifier and 5 kg of calcium carbonate in 8060 kg of dissolving water.

(2) Heating and Sterilizing 10 t of the per os liquid food at 10° C. is put into the storage tank 2, and the per os liquid food is sterilized by a procedure similar to those in Examples 2 and 3.

9.9 t of the sterilized per os liquid food is provided under conditions of a preheating temperature of 125° C., an inlet pressure of the high pressure homogenizer 30 of 0.3 MPa, a homogenizing pressure of the high pressure homogenizer 30 of 100 MPa, a sterilizing temperature of 150° C., an outlet pressure of the high pressure homogenizer 30 of 0.5 MPa, and a post-cooling temperature of 5° C.

With respect to the sterilized per os liquid food, when fat particles are observed similar to Examples 2 and 3, it is confirmed that the sterilizer per os liquid food is sufficiently homogenized, and further, when bacteria count is measured similar to Test 1, bacteria is not detected.

EXAMPLE 5

An explanation will be given of an example of continuous sterilization of milk tea by using a small-sized continuous heat sterilization apparatus according to the invention which is used in Test 2.

(1) Preparation of Milk Tea Drink 500 kg of a milk tea drink is prepared by mixing and dissolving 35.0 kg of skim milk, 10.0 kg of non-salt butter, 30.0 kg of liquid sugar, 250.0 kg of black tea extracted solution and 2.0 kg of a stabilizer in 173.0 kg of dissolving water.

(2) Apparatus

The test apparatus according to the invention (treating amount; 200 l/h type) used in Test 2 is used.

(3) Heating and Sterilizing 500 kg of the milk tea drink is held at 10° C. in the storage tank 2 of the test apparatus, then transmitted to preheating section 10 by a supply amount of 200 l/h by feed pump 3, and sterilized in high pressure homogenizer 30 by respectively setting an inlet temperature to 120° C., an inlet pressure to 0.4 MPa, an outlet pressure to 0.7 MPa, an homogenizing pressure to 90 MPa, a temperature on an outlet side (sterilizing temperature) to 140° C., and a holding time to 2 seconds. Further, the milk tea drink is cooled to 5° C. via first cooling section 40 and the second cooling section 50.

When the apparatus is operated for about 2 hours continuously under these sterilizing conditions, values of the inlet pressure and the outlet pressure of the high pressure homogenizer 30 are not particularly changed and 480 kg of a sterilized milk tea drink can stably be obtained.

COMPARATIVE EXAMPLE 500 kg of a milk tea drink the same as that in Example 5 is sterilized as follows by using a test apparatus of a conventional plate-type sterilizer (200 l/h type, made by Morinaga Engineering Co. Ltd., refer to FIG. 4).

500 kg of the milk tea drink is held at 10° C. in storage tank 2 of the conventional plate-type sterilizer shown by FIG. 4, then transmitted to preheating section 10 by a supply amount of 200 l/h by feed pump 3, and sterilized by setting a homogenizing pressure to 15 MPa in low pressure homogenizer 20, and respectively setting a temperature at final heating section 35 (sterilizing temperature) to 140° C. and a holding time to 2 seconds. Further, the milk tea drink is cooled to 5° C. via first cooling section 40 and second cooling section 50. Further, pressure gages are previously installed before and after the final heating section 35, and pressure loss of the final heating section 35 during operation is measured.

As a result of continuous operation under the above-described conditions, pressure loss of the final heating section 35 starts increasing after about 30 minutes, and pressure loss is rapidly increased after about 1 hour, it Accordingly, it becomes difficult to continue operation, and the operation must be stopped.

Thereafter, after carrying out a water operation sufficiently and stopping the operation, when a plate-type heat exchanger of the final heating section 35 is disengaged and its inside checked, a large amount of scorch is noticed on heat conducting faces of respective plates.

It is found from the comparative example that, whereas a long period of time of continuous operation is difficult when a conventional plate-type sterilizer is used, according to the method or the apparatus of the invention, continuous operation can be carried out for a period of time far longer than that in the conventional sterilizer.

EXAMPLE 6

FIG. 2 is a schematic view showing another example of an apparatus for continuous heat sterilization of liquid according to the invention. In FIG. 2, elements same as those in FIG. 1 or FIG. 4 are attached with notations the same as those in FIG. 1 or FIG. 4, and a detailed explanation of these elements will be omitted.

In FIG. 2, continuous heat sterilization apparatus 1a is installed with temperature sensor 33 (resistance thermometer) at holding pipe 4. Output line 61 of the temperature sensor 33 is connected to controlling device 60 (made by Morinaga Nyugyo Co. Ltd., Studione) and an output line 62 of the controlling device 60 is connected to hydraulic pressure control unit 31. Temperature of liquid is detected by the temperature sensor 33, and a detection value is inputted to the controlling device 60. The controlling device 60 is set previously with a target value of a sterilizing temperature and compares the target value and the detection value inputted from the temperature sensor 33, and calculates an operational amount for making both of these values coincide with each other.

The calculated operational amount is outputted to the hydraulic pressure control unit 31 and homogenizing pressure is regulated. The hydraulic pressure control unit 31 is installed with a hydraulic pressure pump and a hydraulic pressure valve (not illustrated), and a homogenizing pressure is adjusted by adjusting hydraulic pressure. When homogenizing pressure is increased, temperature of liquid coming out from homogenizer or pressurization release apparatus 30 is elevated, and when homogenizing pressure is reduced temperature of liquid is lowered. In this way, temperature of liquid coming out from the homogenizer 30 is automatically controlled to a predetermined sterilizing temperature.

Further, the controlling device 60 records to display the detection value of the temperature sensor 33, and is provided with a function of monitoring and recording whether a sterilizing operation is carried out normally.

EXAMPLE 7

FIG. 3 is a schematic view showing still another example of an apparatus for continuous heat sterilization of liquid according to the invention. In FIG. 3, elements the same as those in FIG. 1, FIG. 2 and FIG. 4 are attached with notations the same as those in these drawings and a detailed explanation of these elements will be omitted.

In FIG. 3, according to continuous heat sterilization apparatus 1b, output line 62 of controlling device 60 is connected to steam regulating valve 15 of preheating section 10. An operational amount calculated at the controlling device 60 is outputted to the steam regulating when an opening amount of the steam regulating valve 15 is increased, temperature of liquid at an outlet of the preheating section 10 is elevated and temperature of liquid at an inlet of homogenizer 30 or pressurization release apparatus is elevated, and as a result, temperature of liquid coming out from the homogenizer 30 is elevated. Further, when an opening of the steam regulating valve 15 is reduced, temperature of liquid at the outlet of the preheating section 10 is lowered and temperature of liquid at the outlet of the homogenizer 30 is lowered, such that temperature of liquid coming out from the homogenizer 30 is also lowered. In this way, temperature of liquid coming out from the homogenizer 30 is automatically controlled to a predetermined sterilizing temperature.

Industrial Applicability

The continuous heat sterilization method and apparatus according to the invention is suitable for heat sterilization the various kinds of liquids, particularly liquid-like food and paste-like food in the food processing field since scorching during a final heating step is dispensed with, and accordingly, a long period of continuous operation is feasible. Furthermore, denaturation of liquid caused by heating is inconsiderable, investment cost and running cost are low, and an amount of processing is enormous.

What is claimed is:

1. A method for continuously heat sterilizing a liquid, comprising:
    preheating a liquid so as to provide a preheated liquid;
    heating said preheated liquid to a sterilizing temperature by
        (i) continuously pressurizing said preheated liquid so as to provide a pressurized preheated liquid, and then
        (ii) continuously releasing said pressurized preheated liquid to a lower pressure within a time period that is sufficient to cause said preheated liquid to be heated to a sterilizing temperature so as provide a depressurized liquid at said sterilizing temperature;
    maintaining said depressurized liquid at said sterilizing temperature for a predetermined period of time; and then cooling said depressurized liquid.

2. The method according to claim 1, wherein
    continuously releasing said pressurized preheated liquid to a lower pressure within a period of time that is sufficient to cause said preheated liquid to be heated to a sterilizing temperature comprises continuously releasing said pressurized preheated liquid to said lower pressure within a time period of less than ten seconds.

3. The method according to claim 2, wherein
    continuously pressurizing said preheated liquid comprises passing said preheated liquid through a high pressure pump.

4. The method according to claim 3, wherein
    passing said preheated liquid through a high pressure pump comprises passing said preheated liquid through a high pressure pump of a homogenizer, and
    continuously releasing said pressurized preheated liquid to a lower pressure comprises using said homogenizer to continuously release said pressurized preheated liquid to said lower pressure.

5. The method according to claim 4, wherein
passing said preheated liquid through a high pressure pump of a homogenizer comprises passing said preheated liquid through said high pressure pump of said homogenizer to continuously pressurize said preheated liquid to a pressure within a range of from 50 Mpa to 100 Mpa.

6. The method according to claim 5, wherein
using said homogenizer to continuously release said pressurized preheated liquid to said lower pressure comprises using said homogenizer to continuously release said pressurized preheated liquid to said lower pressure such that provided is said depressurized liquid at a temperature within a range of from 90° C. to 160° C.

7. The method according to claim 4, wherein
using said homogenizer to continuously release said pressurized preheated liquid to said lower pressure comprises using said homogenizer to continuously release said pressurized preheated liquid to said lower pressure such that provided is said depressurized liquid at a temperature within a range of from 90° C. to 160° C.

8. The method according to claim 3, wherein
continuously releasing said pressurized preheated liquid to a lower pressure comprises continuously releasing said pressurized preheated liquid to said lower pressure such that provided is said depressurized liquid at a temperature within a range of from 90° C. to 160° C.

9. The method according to claim 3, wherein
continuously pressurizing said preheated liquid comprises continuously pressurizing said preheated liquid to a pressure within a range of from 50 Mpa to 100 Mpa.

10. The method according to claim 9, wherein
continuously releasing said pressurized preheated liquid to a lower pressure comprises continuously releasing said pressurized preheated liquid to said lower pressure such that provided is said depressurized liquid at a temperature within a range of from 90° C. to 160° C.

11. The method according to claim 2, wherein
continuously pressurizing said preheated liquid comprises continuously pressurizing said preheated liquid to a pressure within a range of from 50 Mpa to 100 Mpa.

12. The method according to claim 11, wherein
continuously releasing said pressurized preheated liquid to a lower pressure comprises continuously releasing said pressurized preheated liquid to said lower pressure such that provided is said depressurized liquid at a temperature within a range of from 90° C. to 160° C.

13. An apparatus for continuously heat sterilizing liquid, comprising:
a preheating section for preheating a liquid so as to provide a preheated liquid;
a pressurization release device for continuously pressurizing the preheated liquid so as to provide a pressurized preheated liquid, and for continuously releasing the pressurized preheated liquid to a lower pressure within a time period that is sufficient to cause the preheated liquid to be heated to a sterilizing temperature so as provide a depressurized liquid at the sterilizing temperature;
a holding section for maintaining the depressurized liquid at the sterilizing temperature for a predetermined period of time; and
a cooling section for cooling the depressurized liquid after being maintained at the sterilizing temperature by said holding section.

14. The apparatus according to claim 13, wherein
said pressurization release device is for continuously releasing the pressurized preheated liquid to a lower pressure within a time period that is sufficient to cause the preheated liquid to be heated to a sterilizing temperature by releasing the pressurized preheated liquid to the lower pressure within a time period that is less than ten seconds.

15. The apparatus according to claim 14, wherein
said pressurization release device comprises a high pressure pump for continuously pressurizing the preheated liquid, and also comprises a throttle valve for continuously releasing the pressurized preheated liquid to the lower pressure, and
said holding section comprises a holding pipe for maintaining the depressurized liquid at the sterilizing temperature.

16. The apparatus according to claim 15, further comprising:
a storage tank for storing the liquid; and
a feed pump for feeding the liquid from said storage tank to said preheating section.

17. The apparatus according to claim 16, wherein
said high pressure pump is for continuously pressurizing the preheated liquid by continuously pressurizing the preheated liquid to a pressure within a range of from 50 Mpa to 100 Mpa, and
said throttle valve is for continuously releasing the pressurized preheated liquid to the lower pressure such that provided is the depressurized liquid at a temperature within a range of from 90° C. to 160° C.

18. The apparatus according to claim 16, further comprising:
a temperature sensor at said holding pipe for detecting a temperature of the depressurized liquid discharged from said throttle valve;
a control device for comparing the temperature detected by said temperature sensor with a target sterilizing temperature; and
a pressure regulating device for controlling said high pressure pump so as to increase or decrease pressurization of the preheated liquid in accordance with the comparison between the temperature detected by said temperature sensor and the target sterilizing temperature as performed by said control device, whereby the temperature of the depressurized liquid discharged from said throttle valve is increased or decreased such that the temperature detected by said temperature sensor and the target sterilizing temperature are made to approximate each other.

19. The apparatus according to claim 18, wherein
said pressurization release device comprises a homogenizer.

20. The apparatus according to claim 16, further comprising:
a temperature sensor at said holding pipe for detecting a temperature of the depressurized liquid discharged from said throttle valve;
a control device for comparing the temperature detected by said temperature sensor with a target sterilizing temperature; and
a temperature regulating device for regulating a temperature of an inlet of said high pressure pump so as to increase or decrease a temperature of the preheated liquid at the inlet of said high pressure pump in accordance with the comparison between the temperature detected by said temperature sensor and the target sterilizing temperature as performed by said control device, whereby the temperature of the depressurized liquid discharged from said throttle valve is increased or decreased such that the temperature detected by said temperature sensor and the target sterilizing temperature are made to approximate each other.

21. The apparatus according to claim 20, wherein said pressurization release device comprises a homogenizer.

22. The apparatus according to claim 16, wherein said pressurization release device comprises a homogenizer.

23. The apparatus according to claim 14, wherein said pressurization release device is for continuously pressurizing the preheated liquid by continuously pressurizing the preheated liquid to a pressure within a range of from 50 Mpa to 100 Mpa, and is for continuously releasing the pressurized preheated liquid to the lower pressure such that provided is the depressurized liquid at a temperature within a range of from 90° C. to 160° C.

24. The apparatus according to claim 13, wherein said pressurization release device is for continuously pressurizing the preheated liquid by continuously pressurizing the preheated liquid to a pressure within a range of from 50 Mpa to 100 Mpa, and is for continuously releasing the pressurized preheated liquid to the lower pressure such that provided is the depressurized liquid at a temperature within a range of from 90° C. to 160° C.

25. The apparatus according to claim 13, further comprising:

a temperature sensor at said holding section for detecting a temperature of the depressurized liquid discharged from said pressurization release device;

a control device for comparing the temperature detected by said temperature sensor with a target sterilizing temperature; and a pressure regulating device for controlling said pressurization release device so as to increase or decrease pressurization of the preheated liquid in accordance with the comparison between the temperature detected by said temperature sensor and the target sterilizing temperature as performed by said control device, whereby the temperature of the depressurized liquid discharged from said pressurization release device is increased or decreased such that the temperature detected by said temperature sensor and the target sterilizing temperature are made to approximate each other.

26. The apparatus according to claim 13, further comprising:

a temperature sensor at said holding section for detecting a temperature of the depressurized liquid discharged from said pressurization release device;

a control device for comparing the temperature detected by said temperature sensor with a target sterilizing temperature; and a temperature regulating device for regulating a temperature of an inlet of said pressurization release device so as to increase or decrease a temperature of the preheated liquid at the inlet of said pressurization release device in accordance with the comparison between the temperature detected by said temperature sensor and the target sterilizing temperature as performed by said control device, whereby the temperature of the depressurized liquid discharged from said pressurization release device is increased or decreased such that the temperature detected by said temperature sensor and the target sterilizing temperature are made to approximate each other.

* * * * *